US012765934B2

(12) United States Patent
Llauradó Ricote et al.

(10) Patent No.: US 12,765,934 B2
(45) Date of Patent: Oct. 20, 2026

(54) METHODS AND SYSTEMS FOR DETERMINING FREEZING OF SKIN DURING COOLING

(71) Applicant: HIGH TECHNOLOGY PRODUCTS, S.L., Barcelona (ES)

(72) Inventors: Albert Llauradó Ricote, Barcelona (ES); José Miguel Moreno Vilafranca, Barcelona (ES); Jorge Villena García, Barcelona (ES); David Belmonte, Barcelona (ES); Gregorio Viera Mármol, Barcelona (ES); Noelia Vaquero Gallardo, Barcelona (ES)

(73) Assignee: HIGH TECHNOLOGY PRODUCTS, S.L., Barcelona (ES)

( * ) Notice: Subject to any disclaimer, the term of this patent is extended or adjusted under 35 U.S.C. 154(b) by 200 days.

(21) Appl. No.: 18/495,982

(22) Filed: Oct. 27, 2023

(65) Prior Publication Data

US 2024/0065746 A1 Feb. 29, 2024

Related U.S. Application Data

(63) Continuation of application No. PCT/EP2022/061241, filed on Apr. 27, 2022.

(30) Foreign Application Priority Data

Apr. 28, 2021 (EP) .................................... 21382374

(51) Int. Cl.
*A61B 18/02* (2006.01)
*A61B 18/00* (2006.01)
*A61F 7/02* (2006.01)

(52) U.S. Cl.
CPC ................ *A61B 18/02* (2013.01); *A61F 7/02* (2013.01); *A61B 2018/00875* (2013.01); *A61B 2018/0231* (2013.01); *A61F 2007/029* (2013.01)

(58) Field of Classification Search
CPC .......... A61B 18/02; A61B 2018/00875; A61B 2018/0231; A61B 2018/0237; A61F 7/02;
(Continued)

(56) References Cited

U.S. PATENT DOCUMENTS 7,367,341 B2 5/2008 Anderson et al.
9,737,434 B2 * 8/2017 Allison .................... A61F 7/10
(Continued)

FOREIGN PATENT DOCUMENTS

CN 112220551 A1 1/2021
WO 2007093998 A1 8/2007
(Continued)

OTHER PUBLICATIONS

European Communication, EP22728044.3, Apr. 5, 2024, 39 pages.
(Continued)

*Primary Examiner* — Beverly M Flanagan
(74) *Attorney, Agent, or Firm* — Edell, Shapiro & Finnan, LLC

(57) ABSTRACT

The disclosure relates to applicators, cooling systems incorporating such applicators, and methods for a cooling treatment of a skin fold of a subject. Methods for determining a freezing event include measuring electrical impedance between a contact plate of an applicator and a return electrode. Methods include determining possible movements as well, which may also be based on measurements of electrical impedance.

20 Claims, 6 Drawing Sheets

(58) Field of Classification Search
CPC ........ A61F 2007/029; A61F 2007/0225; A61F 2007/0239
USPC ........................................................... 607/96
See application file for complete search history.

(56) References Cited

U.S. PATENT DOCUMENTS

| | | | | |
|---|---|---|---|---|
| 12,070,411 | B2 * | 8/2024 | Levinson | A61F 7/10 |
| 2002/0004948 | A1 | 1/2002 | Son | |
| 2012/0002251 | A1 | 1/2012 | Horrall et al. | |
| 2013/0310907 | A1 | 11/2013 | Rogers et al. | |
| 2014/0303696 | A1 * | 10/2014 | Anderson | A61F 7/02<br>607/104 |
| 2015/0216719 | A1 * | 8/2015 | DeBenedictis | A61N 7/00<br>607/108 |
| 2016/0045755 | A1 | 2/2016 | Chun et al. | |
| 2016/0317346 | A1 | 11/2016 | Kovach | |
| 2020/0038234 | A1 * | 2/2020 | Jimenez Lozano | A61F 7/00 |

FOREIGN PATENT DOCUMENTS

| | | | | |
|---|---|---|---|---|
| WO | WO-2009026471 | A1 * | 2/2009 | A61F 7/02 |
| WO | 2013075016 | A1 | 8/2015 | |
| WO | WO-2022121229 | A1 * | 6/2022 | A61B 18/0206 |

OTHER PUBLICATIONS

International Search Report, PCT/EP2022/061241, Aug. 31, 2022, 4 pages.
International Preliminary Report on Patentability and the Written Opinion, PCT/EP2022/061241, Mar. 27, 2023, 5 pages.

* cited by examiner

METHODS AND SYSTEMS FOR DETERMINING FREEZING OF SKIN DURING COOLING

CROSS-REFERENCE TO RELATED APPLICATIONS

The present application relates to and claims the benefit and priority to International Patent Application No. PCT/EP2022/061241, filed Apr. 27, 2022, which claims the benefit and priority to European Patent Application No. 21382374.3, filed Apr. 28, 2021.

FIELD

The present disclosure relates to methods and systems for determining of a freezing event of a skin during cooling. The present disclosure particularly relates to applicators of such systems, and to methods for determining a freezing event based on measuring electrical impedance. The present disclosure also relates to methods and systems for treatment, and particularly cosmetic treatment of a subject to locally reduce adipose tissue, and more particularly relates to methods and systems for locally reducing adipose tissue in a safe manner.

BACKGROUND

US 2016/0045755 discloses systems and methods for use in the reduction of fat. In some embodiments, these include an applicator having electrodes that form capacitors to heat tissue.

US 2012/0022518 discloses systems and method enabling delivery of radiofrequency and cryotherapy applications to adipose tissue for reduction and contouring of body fat.

WO 2007/093998 discloses methods and apparatuses for the treatment of adipose tissue. The methods comprise application of ultrasound energy to a region of adipose tissue. In an embodiment, an RF electric field is generated inside a region of adipose tissue together with the ultrasound energy.

US 2002/0049483 discloses a fluid delivery apparatus for introducing a fluid cooling media to a skin surface including a template with a skin interface surface. An energy delivery device is coupled to the template.

Liposuction has been practiced for many years to reduce excess body fat in patients. Much less invasive treatments that aim at locally reducing adipose tissues by applying cold to a skin fold of a subject have now been offered commercially for many years as well. Subcutaneous adipose tissue has been found to be more sensitive to cold than other tissue. By applying cold to the skin, the underlying lipid-rich cells are damaged and disrupted, whereas other tissue is not damaged or less damaged. Over time, the lipid-rich cells die and disappear, through a natural apoptosis process. A cosmetic treatment for locally reducing fat can thereby be provided.

For this sort of cold treatments, treatment devices are known which have one or more applicators including a cavity. Suction may be applied to the cavity to suck in a skin fold of a subject. One or more thermally conductive (metallic) contact plates may be provided on the inside of the cavity. Thermoelectric cooling elements (Peltier elements) may be used to cool down the plates to a low temperature. Even though thermoelectric cooling elements are most widely used, alternative cooling methods based on e.g. cold fluid cooling down the conductive plates may be used as well.

The contact plates may be substantially straight. One or more contact plates may be provided in the cavity of an applicator. A single curved contact plate or multiple curved contact plates to conform to a region of a subject's body may also be used.

Some form of temperature control is usually provided to control the temperature of the contact plates and thereby the temperature of the skin. In some known devices, temperature of the skin may be measured during a treatment. In other known devices instead, temperature of the conductive plates is measured during a treatment.

By sucking in the skin fold, improved contact between the skin and the cooling elements (e.g. metallic contact plates) is achieved. Additionally, by squeezing a skin fold in between metallic plates, local blood flow may be reduced. Thereby supply of heat to the region can be reduced and cooling can be more effective. Applicators are also known that do not rely on suction of the skin fold.

A risk of a painful and severe injury to a patient is related to freezing of the skin or crystal formation in the skin during such a treatment. It is known that around or below 0° C., freezing of the skin can occur depending on the time of exposure.

In order to avoid freezing of the skin, the use of cryoprotectants is known. A cryoprotectant is a substance that can be used to protect biological tissue from freezing damage (i.e. due to large ice crystals forming).

One of the challenges related to the use of cryoprotectants in such cold treatments is related to the effective protection of the skin by a cryoprotectant. In order for the cold treatments to be effective, the treatments may apply temperatures of less than −5° C. or less, e.g. −10° C. or less for the metallic plates during a prolonged period of time, e.g. more than 30 minutes, and more particularly more than 45 minutes and even more than one hour.

U.S. Pat. No. 7,367,341 relates to methods for use in the selective disruption of lipid-rich cells by controlled cooling. Feedback mechanisms are described to be employed in these methods to monitor and control temperature of the skin. Such a feedback mechanism may include e.g. invasive thermocouples to locally measure a temperature. Also, ultrasound imaging, acoustical, optical and mechanical measurements are mentioned for monitoring crystal formation. An electrical feedback device may be used to monitor the change of electric impedance of the epidermis caused by ice formation in the epidermis. None of these monitoring systems, besides the invasive temperature measurement, are explained in detail.

WO 2009/026471 discloses a system of monitoring, or detecting events during the removal of heat from subcutaneous lipid-rich tissue is described. In some examples, the system detects an increase in temperature at a treatment device in contact with the skin of a subject, determines that the increase in temperature is related to a treatment event, and performs an action based on the determination. In some examples, the system shuts off the treatment device, alerts an operator, or reduces the cooling in response to a determined treatment event.

One disadvantage related to some of these prior art systems is that they are complicated and therefore costly to integrate in a system for locally reducing adipose tissue. Another disadvantage related to many of these prior art systems is that a local freezing event of the skin of the subject may go undetected. I.e. if freezing occurs in a portion of the skin that happens to not be in the immediate vicinity of the probe or sensor, freezing may go undetected until freezing has spread. When freezing is detected, damage may already have occurred.

There still exists a need for devices which can provide for a safe and effective treatment of the skin and which avoid or reduce one or more of the forementioned problems.

SUMMARY

In a first aspect, an applicator for a system for cooling a skin portion of a subject is provided. The applicator comprises a cooling element with a cooling surface for entering into contact with the skin portion of the subject for cooling the skin portion of the subject. The cooling element is electrically conductive and the cooling surface has a lower electrical conductivity than a remainder of the cooling element. The cooling system is configured to determine an electrical impedance between the cooling element and a first return electrode configured to be placed on a body of the subject.

With an applicator according to this aspect, electrical impedance may be used to determine a freezing event. With an applicator according to this aspect the electrical impedance is measured between a significant portion of the cooling surface and the first return electrode, rather than a pointwise measurement as known from the prior art. Determination of a freezing event may thus be more reliable than in the prior art.

A lower electrical conductivity means that the electrical conductivity of the surface is at least 30% lower, specifically at least 50% lower than the electrical conductivity of the cooling element. In specific examples, the surface of the cooling element may be substantially electrically non-conductive. Substantially non-conductive as used throughout the present disclosure may be understood to mean an electrical resistivity of 1.000 Ω·cm, or more, specifically 10.000 Ω·cm or more.

In some examples, the cooling element may be a metallic contact plate, optionally an aluminium plate with an anodized aluminium layer as cooling surface. Aluminium has a high thermal conductivity and therefore an effective and efficient cooling element. Anodized aluminium may be relatively easily provided. Its electrical properties vary depending on its composition but it can have with a high electrical resistivity of e.g. $10^9$ Ω·cm or more, even $10^{11}$ Ω·cm or more.

In some examples, an electrical cable for providing an electrical current to the cooling element, wherein the electrical cable is attached to the cooling element with a screw.

In some examples, a current for determining an electrical impedance is less than 35 mA, specifically less than 1 mA, more specifically 0.5 mA or less. Very small currents may be used to measure electrical impedance and therefore a user experience during a cooling treatment is not negatively affected.

In some examples, an applicator may comprise an accelerometer for measuring the movement of the subject. In other examples, electrical impedance between other electrodes may be used to determine a possible movement of a subject, or of the applicator with respect to the subject's skin fold.

In a further aspect, a cooling system for cooling a skin portion of a subject is provided, which comprises a base station, and one or more applicators according to any of the examples disclosed herein. The applicators are configured to be coupled to the base station, optionally via a flexible tube. In examples, such a flexible tube may be configured to provide electric and/or electronic and/or a pneumatic connection between the control base station and applicator.

Control circuits, electrical power supply, and pneumatic systems may be provided in a base station. From the base station, the applicators may be controlled. Measurements (e.g. temperature, impedance) may be measured in the applicators and provided to the base station. In examples, some of the control circuits may be provided in individual applicators.

In some examples, the first return electrode is configured to be placed on an extremity of the subject. In order to improve measurements of electrical impedance, a certain distance between cooling element and return electrode is beneficial. Arms and legs of the subject may be suitable for this purpose, specifically when the cooling treatment is carried out on the abdomen, submental tissue or buttocks.

In some examples, the cooling system may further be configured to determine a freezing of the skin of the subject based on the electrical impedance, specifically on a variation of the electrical impedance. If freezing events are determined based on electrical impedance, the applicator does not require specific additional auxiliary systems for measuring movements.

In some examples, the cooling system may further be configured to determine the freezing of the skin based on a time derivative of the electrical impedance. It has been found that a variation (and specifically time derivatives) of the electrical impedance is a better indicator of freezing event rather than an absolute value of the measured electrical impedance.

Apart from freezing events, also movements may be determined using the electrical impedance. If both movements and freezing events are measured using the same electrical parameter, systems or components may be combined and integrate different functionalities, reducing complexity and reducing independent failures of systems. The system may be configured to determine the movements of the subject or the movements of the skin portion with respect to the cooling element by determining an electrical impedance between a movement sensor electrode and a movement sensor return electrode. Optionally, the movement sensor return electrode may be the first return electrode, i.e. the same electrode used in measurements of the freezing event.

The movement sensor electrode may be arranged in proximity of or around a cavity of the applicator configured to receive a skin fold such that a movement of the applicator with respect to the skin fold may be measured by both systems. If instead only the system involving the cooling element measures a significant event, and the other system for detecting movements does not, the likelihood of an actual event increases. Both false negatives and false positives may be reduced in this manner.

In a further aspect, a method for determining a freezing event during a cooling treatment is provided. A cooling element cools a skin portion of a subject during the cooling treatment. The method comprises determining a first electrical impedance between the cooling element and a first return electrode placed on the subject and determining a time derivative of the determined first electrical impedance. The method further comprises determining movements, including movement of the subject and/or movements of a skin portion of the subject with respect to the cooling element using a mechanism for detecting movement. The method comprises determining the freezing event if the time derivative of the first electrical impedance satisfies one or more freezing conditions during a first time slot, and if distortion of the first electrical impedance due to a movement in the same time slot is discarded.

More than one freezing conditions may be established to reduce false positives. More than one criterion to determine possible movements may be established to reduce false negatives.

A time derivative may be understood as a derivative of a function (in this case the measured first electrical impedance) with respect to time. The time derivative of the determined first electrical impedance, may particularly be the first order time derivative or the second order time derivative.

Distortion due to a movement in the first time slot may be discarded if no indication of a possible movement is derived from the mechanism for detecting movement, or if a possible movement derived from the mechanism for detecting movement is insufficient to cause satisfaction of the freezing conditions.

Throughout the present disclosure, "first time derivative" may be understood as the first order time derivative, i.e. it represents the rate of change of a variable with respect to time. Throughout the present disclosure "first time derivative", "first derivative" and "first order time derivative" may be used interchangeably.

In yet a further aspect, a method for reducing adipose tissue, particularly a cosmetic method for reducing adipose tissue is provided. The method comprises providing a cooling system according to any of the examples disclosed herein, providing contact between a skin portion of the subject and the cooling element of the cooling system and cooling the skin portion of the subject e.g. during a period of up to 70 minutes, 90 minutes, 120 minutes or more. The method also comprises carrying out a method for determining a freezing event as disclosed herein during the cooling.

In examples, the cooling of the skin portion may be interrupted if a freezing event is detected and/or an alarm may be generated and/or temporary heating (instead of cooling) may be carried out to avoid damage to the subject's skin.

In examples, the method may further comprise checking correct functioning of the cooling system by determining the electrical impedance between the cooling element and a first return electrode and/or by determining the electrical impedance between the movement electrode and the movement return electrode. If appropriate contact with the skin is provided, electrical impedance will be within an expected range. Such a measurement may be used during, or at the beginning or even prior to starting a cooling treatment to determine that the skin fold is in contact with the contact plates. If a cryoprotectant (pad) is used, proper placement of the cryoprotectant pad may be checked by measuring electrical impedance as well.

Throughout the present disclosure, the term "skin" when used in relation with a freezing event may refer to dermis, epidermis or both.

BRIEF DESCRIPTION OF THE DRAWINGS

Non-limiting examples of the present disclosure will be described in the following, with reference to the appended drawings, in which.

DETAILED DESCRIPTION

Figure 1:
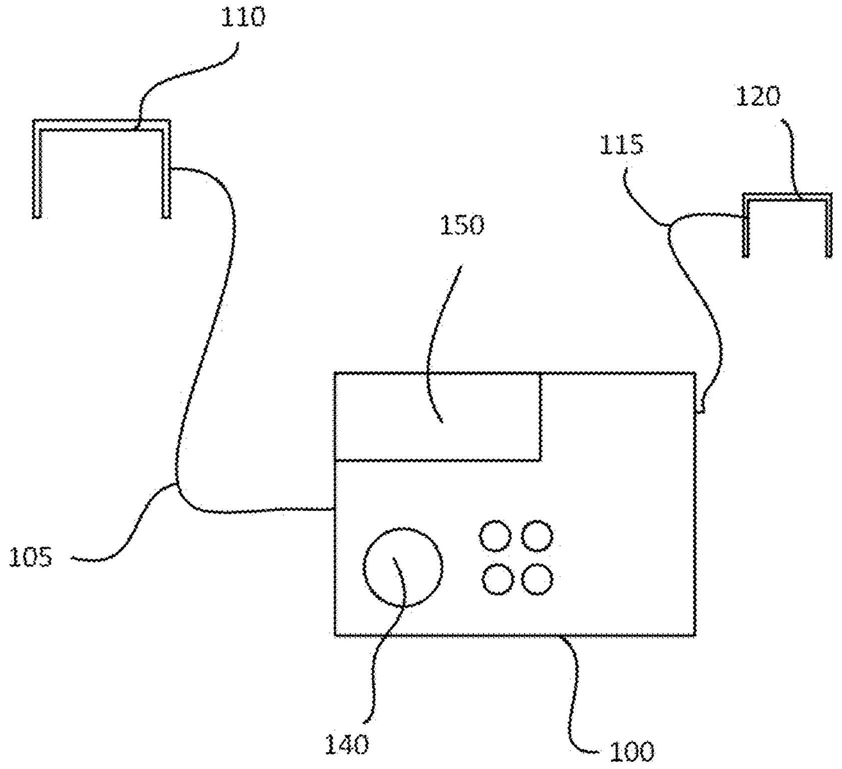
FIG. 1 schematically illustrates an example of a cooling system.

FIG. 1 schematically illustrates an example of a cooling system which may be used in a method for reducing adipose tissue, particularly a cosmetic method for reducing adipose tissue.

The method may comprise providing a cooling system as illustrated in FIG. 1. The cooling system of FIG. 1 comprises a base station 100 and one or more applicators 110, 120. The base station may include a user interface 150 including a screen which may indicate information regarding the cooling treatment.

The user interface 150 may include a tactile screen. A tactile screen and/or one or more control buttons or handles may be used to select a suitable cooling treatment and/or adjust parameters for the cooling treatment.

The applicators 110, 120 may each be connected to the base station through a flexible tube or hose 105, 115. Such a flexible tube 105, 115 may be configured to provide electric and/or electronic and/or a pneumatic connection between the base station and applicators.

The base station may have an electrical supply, e.g. an electric cable with a plug.

Applicators may have different sizes and shapes adapted for cooling of different parts of a subject's body. In a method for reducing adipose tissue, a skin fold of a subject may be introduced in a cavity of the applicator and a portion of the skin of the subject may be brought into contact with a cooling element of the applicator.

A cooling treatment may include cooling the skin portion of the subject during a period of up to 90 minutes. Depending on the skin portion to be cooled, and depending on the objective of the treatment, duration and other settings (e.g. temperature) may be varied.

In examples, cooling the skin portion comprises controlling a temperature of the cooling element to between 0 and −15° C., specifically between −5° C. and −13° C. The skin portion of the subject may be one or more of thigh, buttocks, abdomen, submental tissue, knees, back, face, and arms. A cooling system may include a plurality of applicators and a plurality of skin folds can be treated at the same time.

With temperatures below 0° C. for a prolonged period of time, freezing of the skin may occur. To avoid such freezing, a pad or absorbent with a cryoprotectant may be used. The cryoprotectant may be provided between skin and cooling element to protect the skin.

In examples of the present disclosure, throughout a cooling treatment, a method for determining a freezing event may be continuously carried out. If a freezing event is detected, the cooling treatment may be interrupted, or otherwise altered to avoid damage or injury to a subject's skin. The cooling of the skin portion may be interrupted if a freezing event is detected. In examples, a method may include temporarily heating up the cooling elements if a freezing event is detected. In examples, an audible or visual alarm may be generated so that if a freezing event is detected such that an operator can intervene by manually altering the treatment, interrupting the treatment, disconnecting the base station or other.

Figure 2A:
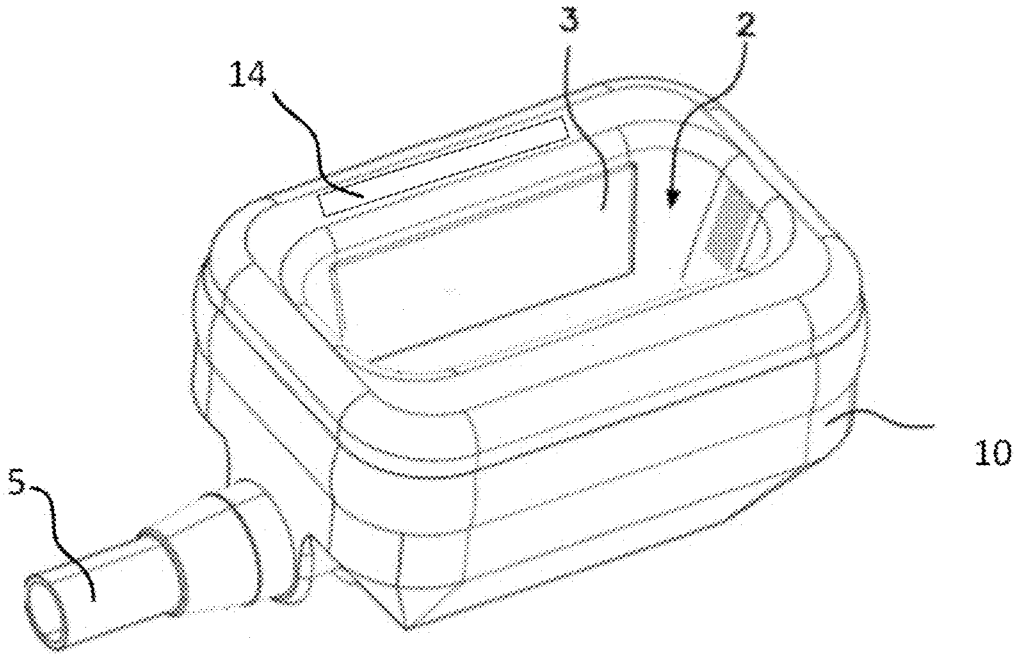
FIGS. 2A and 2B schematically illustrate an example of an applicator and a cooling system including such an applicator.
Figure 2B:
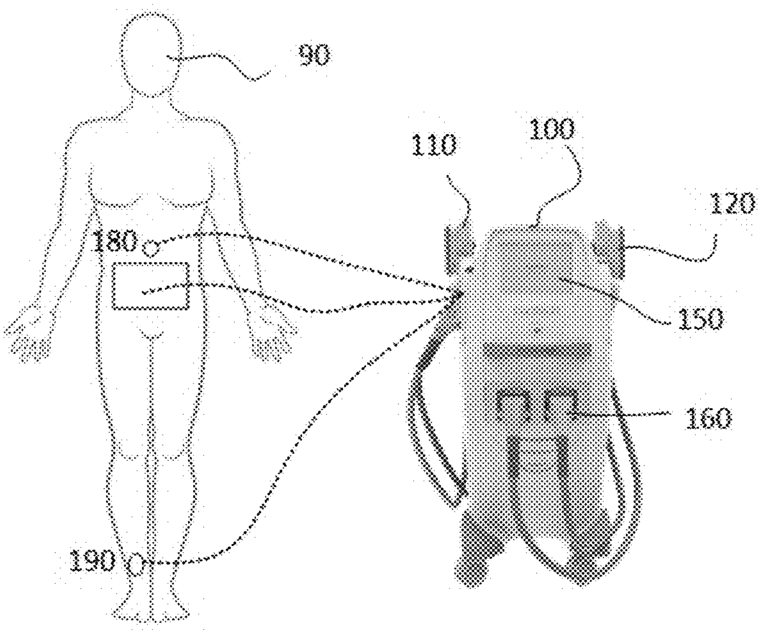

FIGS. 2A and 2B schematically illustrate an example of an applicator 10, and a cooling system for treating a skin fold of a subject 90. As in the example of FIG. 1, the cooling system of FIG. 2B may include a base station 100 with a user interface 150, and multiple applicators 110, 120, 160. The applicators may be similar to the applicator 10 shown in FIG. 2A.

The applicator 10 may include a cavity 2 for receiving a skin fold. An orifice connected to a suction system may be provided in a bottom of the cavity 2. The pump and power for sucking the skin fold into the applicator may be incorporated in the base station. Flexible tube or hose 5 may connect the applicator 10 to a corresponding base station. The applicator 10 may comprise a suitable coupling for coupling to tube 5. Providing suction or a vacuum can help ensure contact between the skin fold to be treated and one or more contact plates 3 arranged within the cavity.

Depending on the skin fold to be treated, the applicator may include one or more straight contact plates, e.g. two contact plates at opposite positions of the cavity. In other examples, a single contact plate which may be curved and/or may be shaped like a cup.

The applicator 10 for a system for cooling a skin portion of a subject comprises a cooling element 3 with a cooling surface for entering into contact with the skin portion of the subject for cooling the skin portion of the subject. The cooling element is electrically conductive and the cooling surface has a lower electrical conductivity than a remainder of the cooling element. The cooling system may be configured to determine an electrical impedance between the cooling element 3 and a first return electrode 190 configured to be placed on a body of the subject.

The cooling element 3 may be a metallic contact plate, optionally an aluminium plate. An aluminium plate may have a relatively good thermal conductivity. The applicator may further comprise a thermoelectric cooler configured to cool the metallic contact plate. Each of the contact plates may be cooled with Peltier elements. By controlling the power supplied to the Peltier elements, the temperature of the contact plates and thus the cooling of the skin fold can be controlled. Temperature sensors may be arranged in contact with the skin, or alternatively may measure temperature of the contact plate, or of the Peltier elements.

The cooling surface may be substantially electrically non-conductive. A higher resistivity of the cooling surface means that the whole contact plate may act as an electrode for impedance measurement. The cooling surface comprises an electrically non-conductive coating. The cooling surface may be an anodized aluminium layer.

The applicator 10 may comprise an electrical cable for providing an electrical current to the cooling element, wherein the electrical cable is attached to the cooling element with a screw. A current for determining an electrical impedance may be less than 35 mA, specifically less than 1 mA, more specifically 0.5 mA or less.

The applicator 10 may further comprise a mechanism for determining a movement. A movement may include a movement of the applicator, a movement of a skin fold with respect to the applicator or a movement of the subject. Such movements can affect the measurement of electrical impedance, and can thus affect the reliability of the determination of a freezing event.

In some examples, the applicator 10 may include an accelerometer for measuring the movement of the subject. In other examples, a further impedance measurement may be used to detect movements.

In some examples, a first return electrode 190 may be configured to be placed on an extremity of the subject. Electrical impedance between the contact plate 3 and first return electrode 190 may be measured to determine a possible freezing of the skin.

The cooling system may be configured to determine a freezing of the skin of the subject based on the electrical impedance, specifically on a variation of the electrical impedance by receiving signals and analysing signals regarding electrical impedance from the applicators.

In examples, the cooling system may be configured to determine the freezing of the skin based on a time derivative of the electrical impedance. It has been found that particularly a variation of the electrical impedance can be a reliable indicator of a freezing event.

In examples, the cooling system is further configured to determine movements of the subject or movements of the skin portion with respect to the cooling element by determining an electrical impedance between a movement sensor electrode 14 (in FIG. 2A) and a movement sensor return electrode. In FIG. 2B, the movement sensor electrode 14 is integrated in an applicator. The movement sensor electrode may be attached to the applicator, e.g. by fasteners such as screw, or by adhesive or any other suitable means. In examples, a kit maybe provided with which an applicator can be upgraded or retrofitted with a suitable system for measuring electrical impedance to determine possible freezing.

In an alternative example, a movement sensor electrode 180 may be separate from an applicator.

In examples, the movement sensor return electrode may be the first return electrode 190 (i.e. the same return electrode used in combination with the contact plate).

Figure 3:
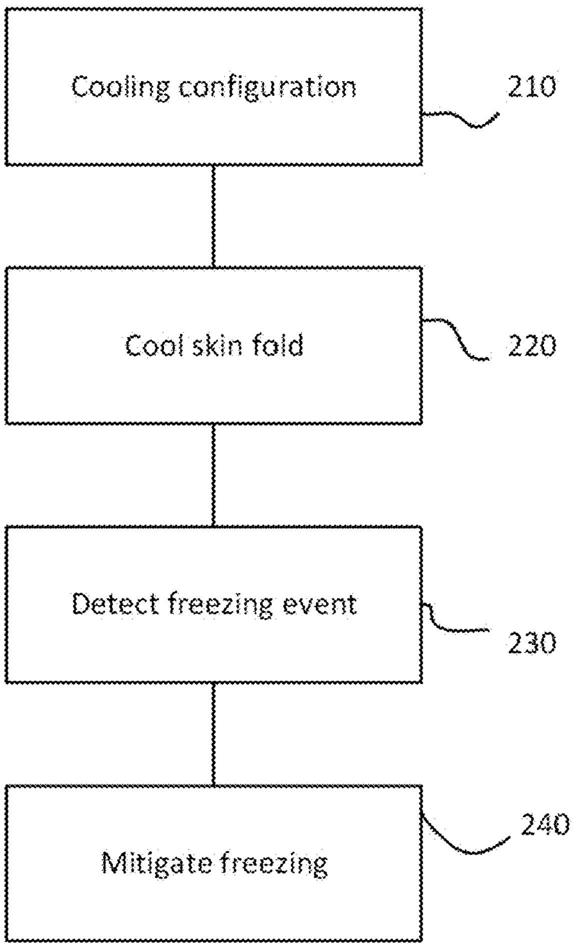
FIG. 3 schematically illustrates a method for reducing adipose tissue according to an example.

FIG. 3 schematically illustrates a method for reducing adipose tissue according to an example. In any of the examples disclosed herein, a skin fold to be treated may be of one of the following areas of the subject: thigh, buttocks, abdomen, submental tissue, knees, back, face, arms. In any of the examples disclosed herein, several skin folds may be treated simultaneously. For example, a single treatment device may comprise more than one applicator, and the applicators may be applied simultaneously to different skin folds.

At block 210, the configuration for the cooling may be determined. The configuration may depend particularly on which body part is treated. Particularly, cooling temperature and cooling time may be configured. Cooling temperature may relate to a temperature of the body of the subject in the treated region (temperature measured e.g. at epidermis), or a temperature of the cooling element.

In examples, contact plates of the treatment device may be maintained at a temperature below 0° C., more particularly below −5° C. for a period between 15 and 90 minutes. Specially, the contact plates may be maintained in contact with the skin for a period between 20 and 75 minutes. The treatment time may be adapted to the area of skin that is being treated. Treatment times for some areas of skin may be for example 30 to 50 minutes, and for other areas of skin, the treatment time may be for example 60 to 75 minutes.

In some examples, the base station of the cooling system may have a number of predefined and stored cooling programs. An operator may simply select the treatment of choice or the body part to be treated. Alternatively, the base station may be able to determine which applicator is activated or is connected to the base station. If the applicator can only be used in a single area, the base station may thus automatically recognize the area or body part is being treated and automatically select the suitable configuration. Alternatively, the base station can recognize the applicator, whereas an operator indicates (e.g. selects on the base station) which specific area, zone or body part will be treated of the different areas or zones which could be treated with the specific applicator.

The skin fold(s) may be introduced into the applicator(s). A cryoprotectant may be arranged between the skin fold and the contact plates in the applicators. At block 220, the skin fold may be cooled particularly with the objective of cooling adipose tissue to locally reduce fat.

During the cooling treatment, continuous monitoring may take place at block 230 to detect a freezing event. If such a freezing event is detected at block 230, the freezing may be mitigated at block 240 in any of a variety of ways commented herein including disconnecting the cooling system, warming up the contact plates (temporarily), shutting of the cooling system and other.

Figure 4:
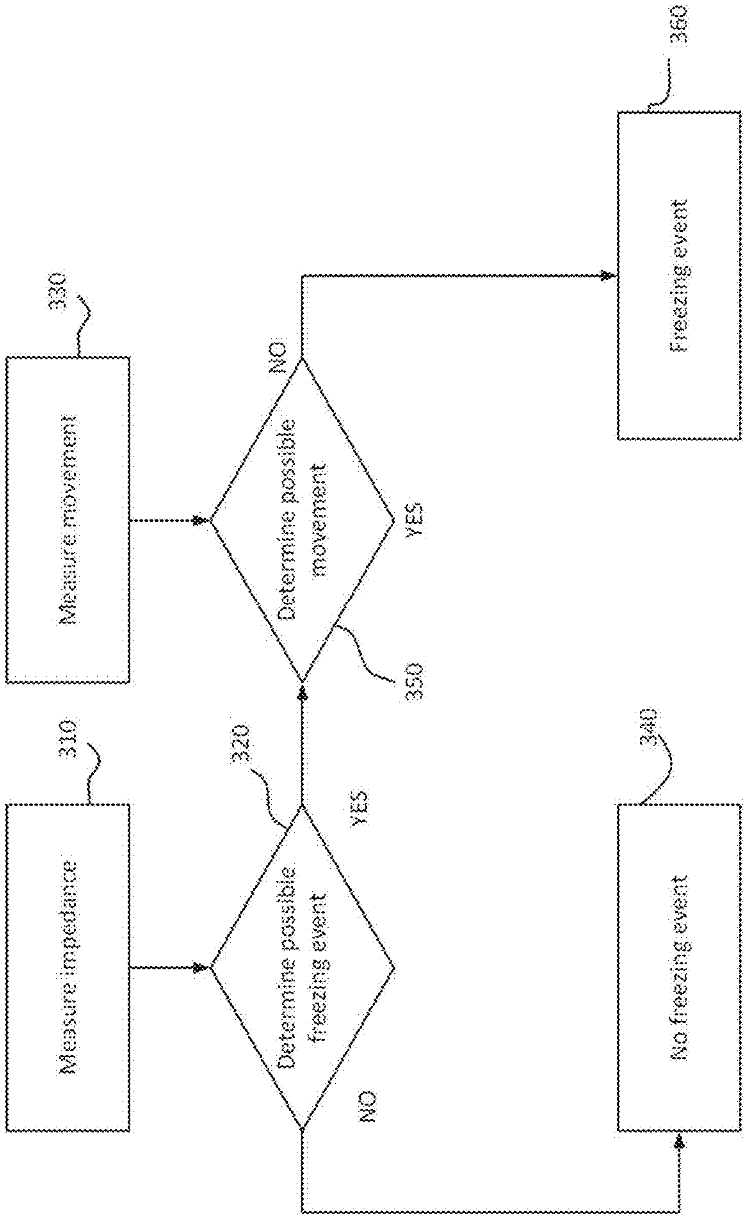
FIG. 4 schematically illustrates a method for determining a freezing event during a cooling treatment according to an example.

FIG. 4 schematically illustrates a method for determining a freezing event during a cooling treatment according to an example. During the cooling treatment, impedance may be measured substantially continuously. Measuring impedance at block 310 means that an electrical impedance is measured between a metal contact plate and a first return electrode. Measuring impedance may be carried out with a frequency of, for example, 1 kHz to 1000 kHz, specifically between 10 kHz and 200 kHz.

At block 320, based on the measured impedance, a possible freezing event of a user's skin may be determined. If the electrical impedance develops in such a way that is not suspicious of a freezing event, the flow diagram passes to block 340 and the conclusion is that there is no freezing event. It should be clear that the method is continuous, i.e. measuring impedance may be performed continuously and thus continuously conclusions may be reached with respect to freezing.

If at block 320, a possible freezing event is detected, a determination may be made whether there is a possible movement at block 350. In examples, movements may be continuously measured at block 330. If electrical impedance measured at block 310 develops in such a way that freezing is detected, and at the same time no movement is detected, the conclusion may be reached at block 360 that there is a freezing event. A reason for checking for possible movement is to reduce false positives because movements can cause similar impedance changes as a freezing event.

In accordance with this example, possible movements may be measured continuously, but an evaluation of the possible movements is only made if a freezing event is suspected.

Figure 5:
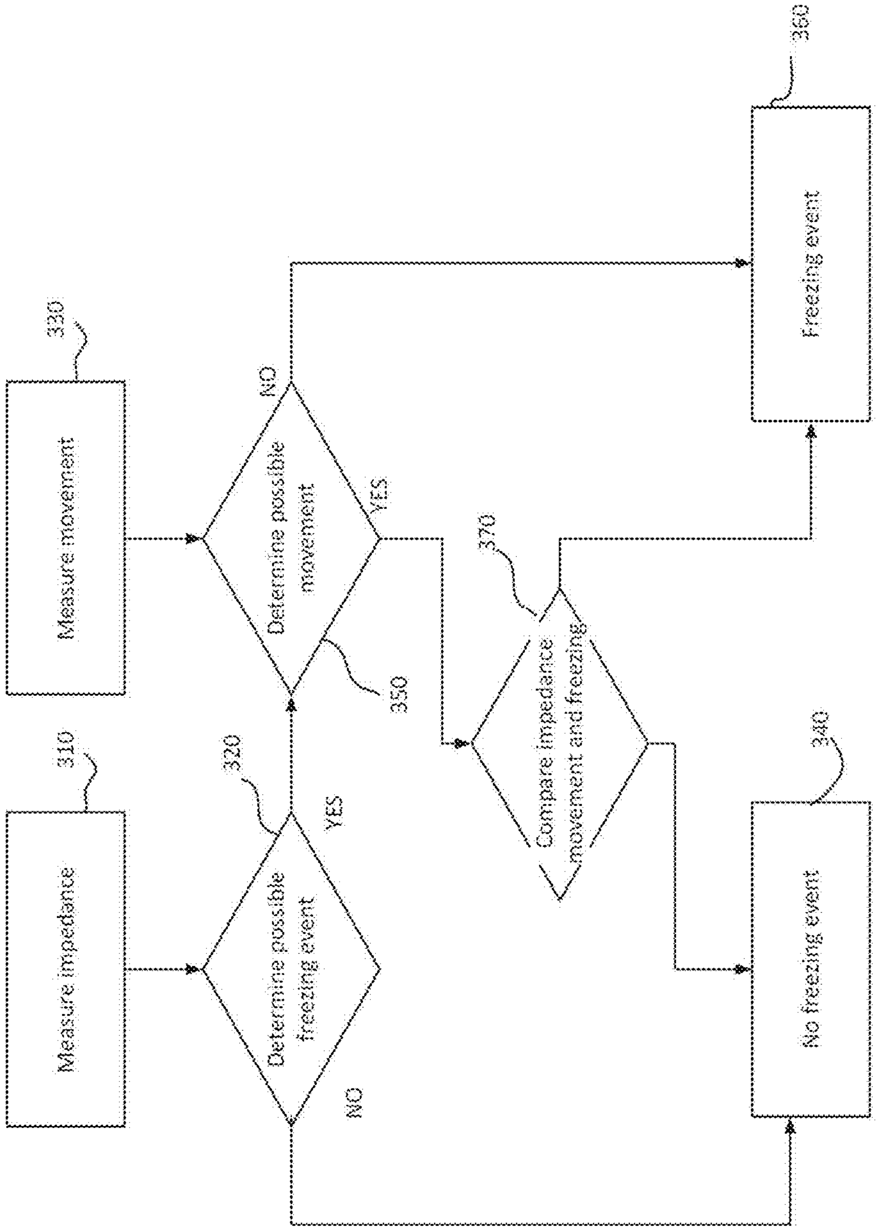
FIGS. 5 and 6 schematically illustrate further examples of methods for determining a freezing event during a cooling treatment.

An alternative example is shown in FIG. 5. As in FIG. 4, movements and electrical impedance between the cooling element and a first return electrode placed on the subject may be continuously measured (blocks 310, 330). Movements may be measured by determining an electrical impedance between a movement sensor electrode and a movement sensor return electrode. The movement sensor return electrode may be the first return electrode.

Independently from one another, and continuously, possible freezing elements may be detected, and possible movements may be detected (blocks 320, 350).

As long as no freezing event is suspected, the conclusion is reached at block 340 that there is no freezing event, and thus no reason to interrupt or modify the cooling treatment. If a freezing event is suspected, it is verified whether a movement might have affected the determination of the freezing event. If at the same time, a freezing element is suspected and the determination is made that a movement cannot have caused this, then the conclusion is reached at block 360 that a freezing event has occurred or is occurring.

In the example of FIG. 5, a further block 370 is introduced. If a freezing event is suspected and at the same a movement is suspected, a further check is made to determine whether there is an actual freezing event or not. At block 370 a further evaluation may be made by comparing the development or variation of electrical impedance measured for movement detection and electrical impedance measured for determining a freezing event. If a freezing event occurs, the electrical impedance may increase in both measurements, but it may be more pronounced between the cooling element and the return electrode.

In any of the examples of FIGS. 4 and 5, a freezing event may be suspected, if one or more freezing conditions are met for the electrical impedance.

In any of the examples, a method for determining a freezing event during a cooling treatment, wherein a cooling element cools a skin portion of a subject comprises determining (block 310) a first electrical impedance between the cooling element and a first return electrode placed on the subject, and determining a time derivative of the determined first electrical impedance.

In particular, the first order time derivative may be used. The first order time derivative indicates a speed of change of the first electrical impedance and has been found to be able to reliably indicate a possible freezing event if the first order time derivative is above a threshold.

In other examples, the second order time derivative may be used. The second order time derivative indicates an acceleration of the first electrical impedance. Outliers over time of the second order time derivative may also indicate a possible freezing event. In one example, an absolute value of the second order time derivative may be compared with a threshold value.

The method may further include determining movements (block 350), including movement of the subject and/or movements of a skin portion of the subject with respect to the cooling element using a mechanism for detecting movement.

A freezing event may be determined if the first order time derivative of the first electrical impedance satisfies one or more freezing conditions during a first time slot, and if distortion of the first electrical impedance due to a movement in the same time slot is discarded. A first freezing condition is that the first order time derivative of the first electrical impedance is above a first freezing threshold during a first time slot.

In some examples, the first freezing threshold is determined based at least partially on measured values of the first time derivative. In examples, the first freezing threshold may vary over time.

Figure 6:
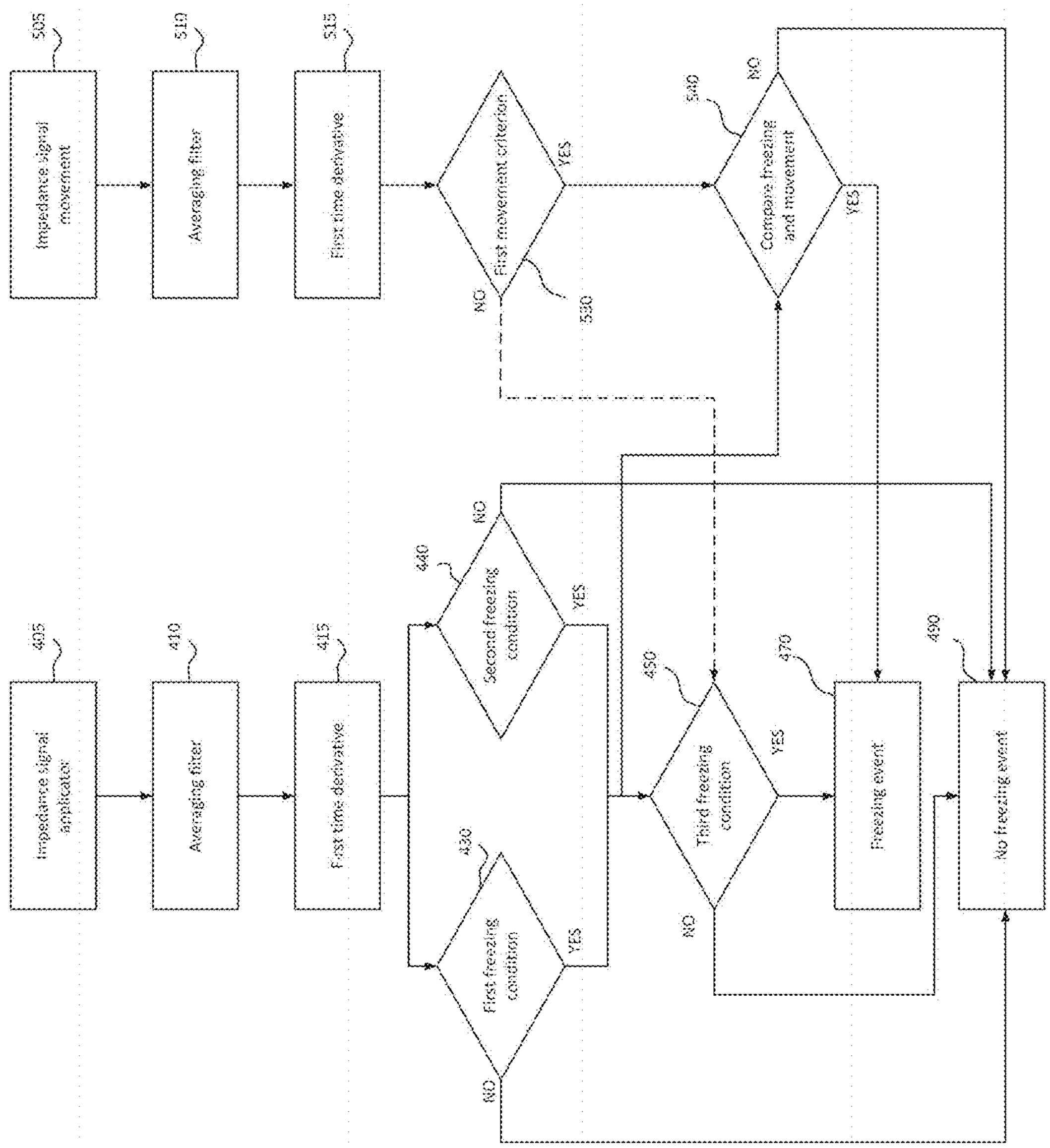

A further example is shown in FIG. 6. At block 405, signals regarding electrical impedance between the cooling element and the first return electrode may be received. A filter may be applied to the received signal, at block 410. Particularly, an averaging filter may be applied, e.g. a number of individual measurement points may be summed and averaged and correlated to a single measurement time (in the middle of the averaged measurement points).

In an example, impedance measurements may be made at a frequency of 1 kHz to 1.000 kHz, and specifically between 50 to 200 kHz, and more specifically around 100 kHz.

The sample time of the averaging filter may be 0.1 seconds to a few seconds, and specifically between 0.5 and 2.5 seconds.

Similarly, at block 505, signals regarding electrical impedance between a movement sensor electrode and the movement return electrode are received. At block 510, a similar averaging filter may be applied. The measurement frequency and averaging may be the same or in the same order of magnitude for the impedance measurement for movements and the impedance measurements for detecting potential freezing events.

After filtering, at blocks 415, 515, a time derivative of both measurements may be determined, in particular a first order time derivative. A plurality of freezing conditions may be defined for the first order time derivative of the electrical impedance at blocks 430 and 440.

A first freezing condition, block 430, may be that the first order time derivative of the first electrical impedance is above a first freezing threshold, or between predefined first freezing thresholds during a first time slot. The freezing threshold thus corresponds to a value of rate of change of the electrical impedance. In some examples, the first freezing threshold may vary over time. Optionally, not individual values of the first order time derivative may be compared with the threshold, but rather an average value of two or more moments in time.

In one example:

$$\text{Impedance\_variation}=(\text{current impedance variation}-\text{last impedance variation})/2 \quad \text{(Eq. 1)}$$

$$\text{Peak}=\text{impedance\_variation}/\text{first\_threshold\_value} \quad \text{(Eq. 2)}$$

$$\text{First\_threshold\_value}=(\text{fixed\_threshold}*\text{gain\_threshold})+(\text{abs}[\text{impedance\_variation}]*\text{gain\_impedance}) \quad \text{(Eq. 3)}$$

Equation 1 expresses an averaging over two time slots of the first order time derivative of the electrical impedance. Equation 2 defines a peak value as a ratio between the first order time derivative of the electrical impedance and a threshold value. If a peak is at predefined levels, a freezing event may be detected. If a peak is low, then it is unlikely that freezing occurred, because the electrical impedance variation is too low. If the peak is too high, a freezing event is unlikely, because there must be another cause for a very rapid variation of the electrical impedance (e.g. lost contact between skin and cooling element or similar). Equation 3 indicates how the first threshold value may vary over time taking into account measurements from specific components in a specific cooling treatment.

A second freezing condition may be defined at block 440. A second freezing condition in this example is that an integral of a (natural) logarithmic value of the first order time derivative during a second time slot is above a second freezing threshold, wherein the second time slot is longer than the first time slot.

$$\text{Ln\_value}=\Sigma(\ln(\text{peak})/\text{second time slot} \quad \text{(Eq. 4)}$$

The second time slot may be longer than the first time slot. The first time slot (for the first order time derivative) may be between 1 and 5 seconds, specifically between 1 and 4 seconds. The second time slot may be longer. In an example, the second time slot may be 5 seconds.

If both the first and second freezing conditions are satisfied, then the algorithm passes on to block 450 or block 540 as will hereinafter be explained. If either one of the freezing conditions is not satisfied, the conclusion is drawn at block 490, that no freezing has occurred.

Simultaneously, a first order time derivative of the electrical impedance between movement sensor electrode and return electrode may be determined at block 515, and at block 530, a first movement criterion may be defined.

A possible movement may be derived if a first order time derivative of the electrical impedance between the movement sensor electrode and the movement sensor return electrode during the first time slot is above a movement threshold value, or between predefined movement thresholds (block 530). At block 530, similar Equations 1-3 may be applied but to the signals relating to the movement sensors.

The movement threshold(s) may be determined based at least partially on measured values of the first time derivative. The first movement threshold may vary over time.

If at block 530 no movement is determined or suspected, and at block 430 and 440, freezing is suspected, a third freezing condition may be checked at block 450.

In examples, the first time derivative (particularly of the electrical impedance between cooling element and return electrode) may be determined over time windows with a first span, and over time windows with a second span, the second span being longer than the first span. In practice, different averaging filters may be applied. For example, a first averaging filter based on 32 measurement points may be applied, and at the same time a second averaging filter based on 64 measurements may be applied. It should be clear that 32 and 64 are merely mentioned as examples. In examples, a “Haar” filter is used.

The third freezing condition at block 450 may be defined in that during the first time slot, the first order time derivative determined over the first span (in this example, the averaging filter with 32 points) is substantially different from the first time derivative measured over the second span (the averaging filter with 64 points). If freezing occurs, the first order time derivative with the averaging filter over a shorter time span will be different from the first order time derivative with the averaging filter over the longer time span. If instead the averages are not significantly different, the third freezing condition is not satisfied, and the conclusion is reached at block 490 that there is no freezing event.

If the first and second freezing conditions are satisfied, at blocks 430, 440 and a movement criterion is satisfied at block 530, a further determination may be made whether a movement has distorted the electrical impedance measurement.

In examples, distortion due to a movement in the first time slot may be discarded if no indication of a possible movement is derived from the mechanism for detecting movement, or if a possible movement derived from the mechanism for detecting movement is insufficient to cause satisfaction of the freezing conditions.

The method may thus comprise checking an additional criterion based on the time derivative of the first electrical impedance and on the electrical impedance between the movement sensor electrode and the movement sensor return electrode.

The additional criterion is that a ratio of the time derivative of first electrical impedance and the time derivative of the electrical impedance between the movement sensor electrode and the movement sensor return electrode is above a threshold.

$$\text{Ratio}=\text{Impedance\_variation\_freezing}/\text{impedance\_variation\_movement} \quad \text{(Eq. 5)}$$

If the ratio of Equation 5 is above a specific threshold, this indicates that the first order time derivative of the electrical impedance for freezing is significantly higher than the first order time derivative of the electrical impedance for movement.

In some examples, the additional criterion may be determined (block 540) for the first time slot i.e. the same time slot as for the first and second freezing conditions. In other examples, the additional criterion may be determined after the first time slot.

Figure 7A:
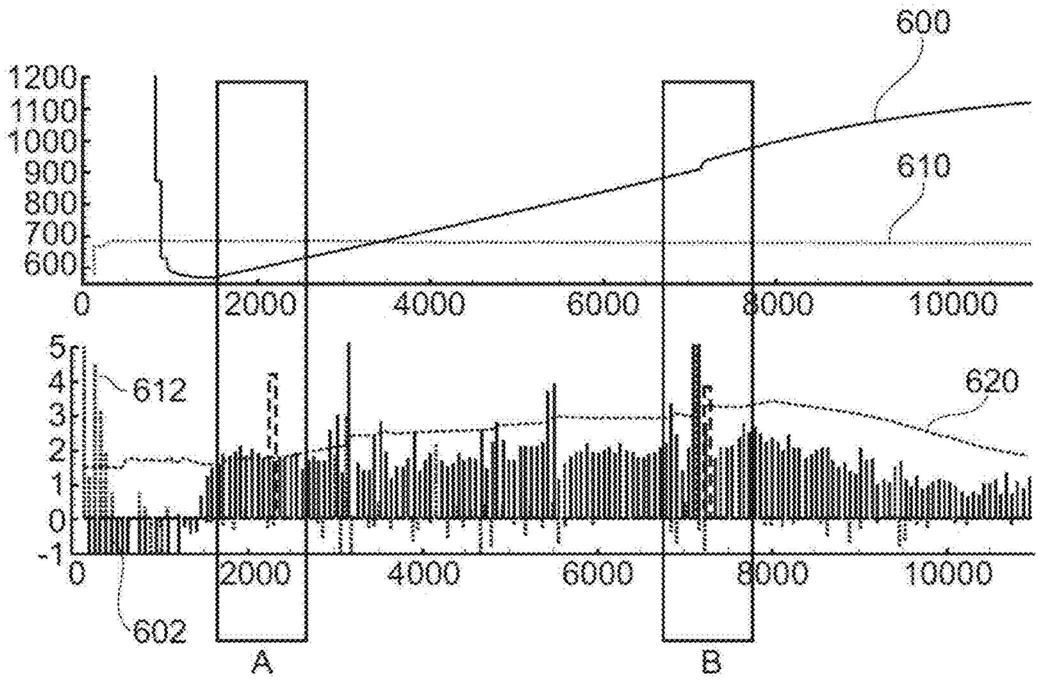
FIGS. 7A and 7B schematically illustrate signals of impedance sensors and a method for evaluating such signals according to an example.
Figure 7B:
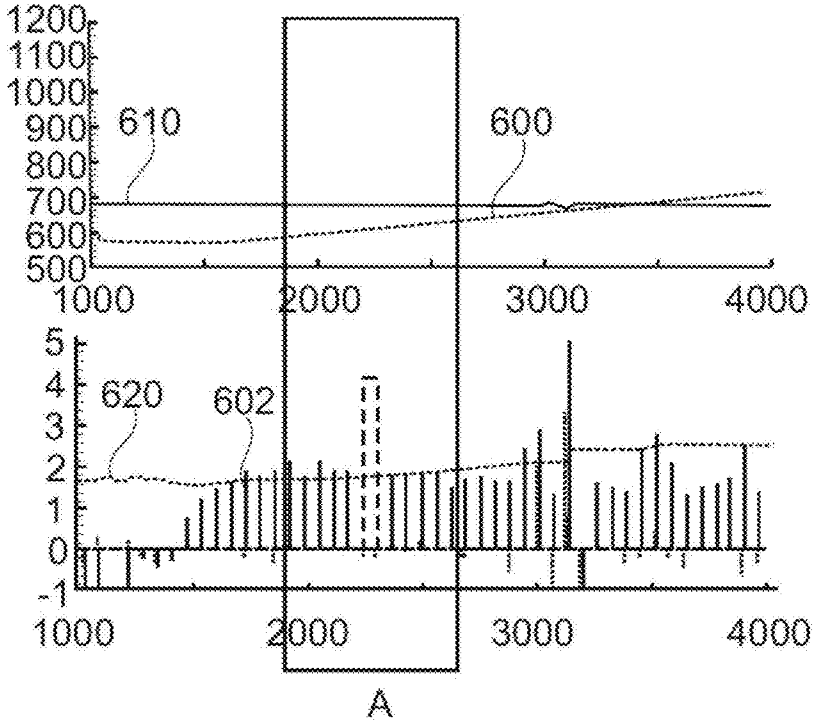

FIGS. 7A and 7B schematically illustrate signals of impedance sensors and a method for evaluating such signals according to an example. In FIG. 7A, at the top part, filtered signals of impedance measurements for freezing (between cooling element and return electrode, reference sign 600) and for movements (between movement electrode and corresponding electrode, reference sign 610) are shown.

After applying the averaging filters and deriving first order time derivatives, the results are shown in the bottom of the figure, with reference signs 602, and 612 respectively. In FIG. 7A, two different time windows have been identified, A, and B in which freezing events may be suspected. Particularly, in window B, specific "jumps" or increases of the electrical impedance may be recognized.

The aforementioned examples of FIGS. 4, 5 and 6 of methods for determining freezing events may be applied to these three time windows as follows.

FIG. 7B illustrates time window A in more detail. Reference sign 620 indicates a threshold for a first order time derivative, which varies over time. With reference to Equations 1-3, the threshold may correspond to a minimum peak value. It may be seen in FIG. 7B that the resulting signals after applying the averaging filter allows identification of specific increases more readily than the unfiltered signals. With reference to the example of FIG. 6, in time window A, a first freezing condition may be found to be satisfied, but a second freezing condition may be found not to be satisfied. The result is that no freezing event is detected and the cooling treatment may continue as normal.

In time window B, first and second freezing conditions may be found to be satisfied. At the same time, also the movement sensor indicates a peak above a corresponding threshold. I.e. at block 530 of FIG. 6, a possible movement is detected because a sufficient increase of electrical impedance is also measured between movement sensor electrode and return electrode. Applying the example of FIG. 6, the algorithm would pass to block 540, and a comparison may be made of the first order time derivative of both electrical impedances. In the case of time window B, the ratio as defined in Equation 5 may be found to be satisfied and the conclusion can be reached that a freezing event has occurred or is occurring.

Measurements of the electrical impedance sensor(s) may also be used to determine a correct positioning of the applicator and skin fold. If measurements of the sensor(s) indicate an unusual pattern, particularly at the beginning of a treatment, this may indicate that the applicator is not correctly positioned, a cryoprotectant pad is not suitably positioned, or another problem and therefore that the skin of the user is not adequately protected and/or that the cooling treatment will not be effective.

Examples of the methods disclosed herein may be implemented with hardware, software, firmware and combinations thereof.

Those of skill in the art would further appreciate that the various illustrative logical blocks, modules, circuits, and algorithm steps described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application.

The various illustrative logical blocks, modules, and circuits described in connection with the disclosure herein may be implemented or performed with one or more general-purpose processors, a digital signal processor (DSP), cloud computing architecture, an application specific integrated circuit (ASIC), a field programmable gate array (FPGA) or other programmable logic device (PLC), discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Various aspects of the present disclosure are set out in the following numbered clauses:

Clause 1. An applicator for a system for cooling a skin portion of a subject, the applicator comprising:

- a cooling element with a cooling surface for entering into contact with the skin portion of the subject for cooling the skin portion of the subject,
- wherein the cooling element is electrically conductive and the cooling surface has a lower electrical conductivity than a remainder of the cooling element, wherein
- the cooling system is configured to determine an electrical impedance between the cooling element and a first return electrode configured to be placed on a body of the subject.

Clause 2. The applicator according to clause 1, wherein the cooling element is a metallic contact plate, optionally an aluminium plate.

Clause 3. The applicator according to clause 2, further comprising a thermoelectric cooler configured to cool the metallic contact plate.

Clause 4. The applicator according to clause 2 or 3, wherein the cooling surface is an anodized aluminium layer.

Clause 5. The applicator according to any of clauses 1-4, wherein the cooling surface is substantially electrically non-conductive.

Clause 6. The applicator according to clause 5, wherein the cooling surface comprises an electrically non-conductive coating.

Clause 7. The applicator according to any of clause 1-6, comprising an electrical cable for providing an electrical current to the cooling element, wherein the electrical cable is attached to the cooling element with a screw.

Clause 8. The applicator according to any of clauses 1-7, comprising a cavity configured to receive a skin fold, wherein the cooling element is arranged within the cavity and is configured to cool the skin fold.

Clause 9. The applicator according to any of clauses 1-8, wherein a current for determining an electrical impedance is less than 35 mA, specifically less than 1 mA, more specifically 0.5 mA or less.

Clause 10. The applicator according to any of clauses 1-9, comprising an accelerometer for measuring the movement of the subject.

Clause 11. A cooling system for cooling a skin portion of a subject comprising a base station, and one or more applicators according to any of clauses 1-10 configured to be coupled to the base station.

Clause 12. The cooling system of clause 11, wherein the applicators are coupled to the base station with a flexible tube.

Clause 13. The cooling system of clause 12, wherein the flexible tube is configured to provide electric and/or electronic and/or a pneumatic connection between the control base station and applicator.

Clause 14. The cooling system of any of clauses 11-13, wherein the first return electrode is configured to be placed on an extremity of the subject.

Clause 15. The cooling system according to any of clauses 11-14, further configured to determine a freezing of the skin of the subject based on the electrical impedance, specifically on a variation of the electrical impedance.

Clause 16. The cooling system according to clause 15, wherein the cooling system is further configured to determine the freezing of the skin based on a time derivative of the electrical impedance.

Clause 17. The cooling system according to any of clauses 11-16, wherein the cooling system is further configured to determine movements of the subject or movements of the skin portion with respect to the cooling element.

Clause 18. The cooling system according to clause 17, wherein the system is configured to determine the movements of the subject or the movements of the skin portion with respect to the cooling element by determining an electrical impedance between a movement sensor electrode and a movement sensor return electrode.

Clause 19. The cooling system according to clause 18, wherein the movement sensor return electrode is the first return electrode.

Clause 20. The cooling system according to clause 18 or 19, wherein the movement sensor electrode is arranged on the applicator.

Clause 21. The cooling system according to clause 20, wherein the movement sensor electrode is arranged in proximity of or around a cavity of the applicator configured to receive a skin fold.

Clause 22. The system according to clause 20 or 21, wherein the movement sensor electrode is attached to the applicator, specifically with adhesive or fasteners.

Clause 23. A method for determining a freezing event during a cooling treatment, wherein a cooling element cools a skin portion of a subject, the method comprising:

determining a first electrical impedance between the cooling element and a first return electrode placed on the subject, determining a time derivative of the determined first electrical impedance, determining movements, including movement of the subject and/or movements of a skin portion of the subject with respect to the cooling element using a mechanism for detecting movement, determining the freezing event if the time derivative of the first electrical impedance satisfies one or more freezing conditions during a first time slot, and if distortion of the first electrical impedance due to a movement in the same time slot is discarded.

Clause 24. The method of clause 23, wherein the time derivative of the determined first electrical impedance is a second order time derivative of the first electrical impedance.

Clause 25. The method of clause 23, wherein the time derivative of the determined first electrical impedance is a first order time derivative of the first electrical impedance, Clause 26. The method of clause 25, wherein a first freezing condition is that the first order time derivative of the first electrical impedance is above a first freezing threshold during a first time slot.

27. The method of clause 26, wherein the first freezing threshold is determined based at least partially on measured values of the first time derivative.

Clause 28. The method of clause 27, wherein the first freezing threshold varies over time.

Clause 29. The method of any of clauses 26-28, wherein a second freezing condition is that an integral of a logarithmic value of the first order time derivative during a second time slot is above a second freezing threshold, wherein the second time slot is longer than the first time slot.

Clause 30. The method of any of clauses 26-29, wherein the first order time derivative is determined over time windows with a first span, and over time windows with a second span, the second span being longer than the first span.

Clause 31. The method according to clause 30, wherein a third freezing condition is that during the first time slot, the first time derivative determined over the first span is substantially different from the first time derivative measured over the second span.

Clause 32. The method according to any of clauses 23-31, wherein distortion due to a movement in the first time slot is discarded if no indication of a possible movement is derived from the mechanism for detecting movement, or if a possible movement derived from the mechanism for detecting movement is insufficient to cause satisfaction of the freezing conditions.

Clause 33. The method of any of clauses 23-32, wherein detecting a possible movement comprises determining an electrical impedance between a movement sensor electrode and a movement sensor return electrode.

Clause 34. The method of clause 33, wherein the movement sensor return electrode is the first return electrode.

Clause 35. The method of clause 33 or 34, wherein a possible movement is derived if a first order time derivative of the electrical impedance between the movement sensor electrode and the movement sensor return electrode during the first time slot is above a movement threshold value.

Clause 36. The method of clause 35, wherein the movement threshold is determined based at least partially on measured values of the first order time derivative.

Clause 37. The method of clause 36, wherein the movement threshold varies over time.

Clause 38. The method of any of clauses 35-37, further comprising checking an additional criterion based on the time derivative of the first electrical impedance and on the electrical impedance between the movement sensor electrode and the movement sensor return electrode.

Clause 39. The method of clause 38, wherein the additional criterion is that a ratio of the time derivative of first electrical impedance and the time derivative of the electrical impedance between the movement sensor electrode and the movement sensor return electrode is above a threshold.

Clause 40. The method of clause 39, wherein the additional criterion is determined for the first time slot.

Clause 41. The method of clause 39, wherein the additional criterion is determined after the first time slot.

Clause 42. A method for reducing adipose tissue, particularly a cosmetic method for reducing adipose tissue, comprising:

providing a cooling system according to any of clauses 11-22;

providing contact between a skin portion of the subject and the cooling element of the cooling system;

cooling the skin portion of the subject optionally during a period of up to 90 minutes; and carrying out the method according to any of clauses 23-41 during the cooling.

Clause 43. The method of clause 42, wherein cooling the skin portion comprises controlling a temperature of the cooling element to between 0 and −15° C., specifically between −5° C. and −13° C.

Clause 44. The method of clause 42 or 43, wherein the cooling of the skin portion is interrupted if a freezing event is detected.

Clause 45. The method of any of clauses 42-44 comprising temporarily heating up the cooling elements if a freezing event is detected.

Clause 46. The method of any of clauses 42-45, wherein an alarm is generated if a freezing event is detected.

Clause 47. The method of any of clauses 42-46, wherein the skin portion of the subject is one or more of thigh, buttocks, abdomen, submental tissue, knees, back, face, arms.

Clause 48. The method of any of clauses 42-47, further comprising checking correct functioning of the cooling system by determining the electrical impedance between the cooling element and a first return electrode and/or by determining the electrical impedance between the movement electrode and the movement return electrode.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow.

The invention claimed is:

1. A cooling system for reducing adipose tissue in a subject by cooling a skin portion of the subject, the cooling system comprising;

a base station;

an applicator that includes an electrically conductive cooling element having a cooling surface that is configured to contact the skin portion of the subject for the purpose of cooling the skin portion of the subject, the cooling surface of the cooling element being substantially electrically non-conductive having an electrical resistivity of 1,000 Ω·cm or more; and a controller that is configured to determine a freezing of the skin portion of the subject based on a time derivative of a first electrical impedance between the cooling element and a first return electrode configured to be placed on a body of the subject, the controller also being configured to determine a movement of the subject or a movement of the skin portion with respect to the cooling element by determining an electrical impedance between a movement sensor electrode and a movement sensor return electrode.

2. The cooling system according to claim 1, wherein the cooling element of the applicator is an aluminium contact plate.

3. The cooling system according to claim 2, wherein the cooling surface of the applicator is an anodized aluminium layer.

4. The cooling system according to claim 1, wherein the applicator includes an electrical cable attached to the cooling element and configured to deliver to the cooling element an electrical current of 35 mA or less, the controller being configured to determine the first electrical impedance between the cooling element and the first return electrode when the electrical current of 35 mA or less is delivered to the cooling element.

5. The cooling system according to claim 1, wherein the applicator is coupled to the base station with a flexible tube and wherein the flexible tube is configured to provide an electric and a pneumatic connection between the base station and the applicator.

6. The cooling system of claim 1, wherein the first return electrode is configured to be placed on an extremity of the subject.

7. The cooling system according to claim 1, further comprising a mechanism for detecting the movement of the subject or the movement of the skin portion of the subject, wherein the controller is configured to determine the freezing of the skin portion by:

determining the first electrical impedance between the cooling element and the first return electrode placed on the subject, determining a time derivative of the determined first electrical impedance, determining the movement of the subject or the movement of the skin portion of the subject with respect to the cooling element using the mechanism for detecting the movement of the subject or the movement of the skin portion of the subject, determining the freezing of the skin portion if the time derivative of the first electrical impedance satisfies at least one freezing condition during a first time slot, and when a distortion of the first electrical impedance due to the movement of the subject or the movement of the skin portion of the subject in the same time slot is discarded.

8. The cooling system of claim 7, wherein the time derivative of the first electrical impedance is a first order time derivative, and wherein the at least one freezing condition is that the first order time derivative of the first electrical impedance is above a first freezing threshold during a first time slot.

9. The cooling system of claim 8, wherein the first freezing threshold is determined based at least partially on measured values of the first order time derivative.

10. The cooling system according to claim 7, wherein the distortion due to the movement of the subject or the movement of the skin portion of the subject in the first time slot is discarded if no indication of a possible movement is derived from the mechanism for detecting movement, or if a possible movement derived from the mechanism for detecting movement is insufficient to cause satisfaction of the one or more freezing conditions.

11. The cooling system of claim 10, wherein the controller is configured to detect a possible movement if a first order time derivative of the electrical impedance between the movement sensor electrode and the movement sensor return electrode during the first time slot is above a movement threshold value.

12. A method for determining a freezing event during a cooling treatment, wherein a cooling element cools a skin portion of a subject, the method comprising:

determining a first electrical impedance between the cooling element and a first return electrode placed on the subject;

determining a time derivative of the determined first electrical impedance;

determining a movement of the subject or a movement of a skin portion of the subject with respect to the cooling element by determining an electrical impedance between a movement sensor electrode and a movement sensor return electrode; and determining the freezing event exists if the time derivative of the first electrical impedance satisfies one or more freezing conditions during a first time slot, and when a distortion of the first electrical impedance due to the movement of the subject or the movement of the skin portion of the subject in the same time slot is discarded.

13. The method of claim 12, wherein the time derivative of the determined first electrical impedance is a second order time derivative of the first electrical impedance.

14. The method of claim 12, wherein the time derivative of the determined first electrical impedance is a first order time derivative of the first electrical impedance.

15. The method of claim 14, wherein a first freezing condition of the one or more freezing conditions is that the first order time derivative of the first electrical impedance is above a first freezing threshold during the first time slot.

16. The method of claim 15, wherein a second freezing condition of the one or more freezing conditions is that an integral of a logarithmic value of the first order time derivative during a second time slot is above a second freezing threshold, wherein the second time slot is longer than the first time slot.

17. The method of claim 12, wherein the movement sensor return electrode is the first return electrode.

18. The method of claim 12, further comprising interrupting the cooling treatment of the skin portion upon a freezing event being detected.

19. The method of claim 12, further comprising temporarily heating the cooling element upon a freezing event being detected.

20. The method of claim 12, wherein the skin portion of the subject is selected from the group consisting of one or more of a thigh, a buttocks, an abdomen, a submental tissue, a knee, a back, a face and an arm.

* * * * *